United States Patent [19]
Lyons

[11] Patent Number: 5,163,447
[45] Date of Patent: Nov. 17, 1992

[54] FORCE-SENSITIVE, SOUND-PLAYING CONDOM

[76] Inventor: Paul Lyons, 295 Elm St., Southbridge, Mass. 01550-3009

[21] Appl. No.: 728,607

[22] Filed: Jul. 11, 1991

[51] Int. Cl.⁵ .............................................. A61F 6/04
[52] U.S. Cl. .................................... 128/844; 128/883; 446/220
[58] Field of Search ............... 128/842, 844, 885, 886, 128/883, 884; 604/347-353; 446/220-226, 404

[56] References Cited

U.S. PATENT DOCUMENTS

| | | | |
|---|---|---|---|
| 494,436 | 3/1893 | Orth | 128/883 |
| 745,264 | 11/1903 | Todd | 128/886 X |

FOREIGN PATENT DOCUMENTS

| | | | |
|---|---|---|---|
| 680088 | 10/1952 | United Kingdom | 128/886 |
| 2036560 | 7/1980 | United Kingdom . | |

OTHER PUBLICATIONS

Frederick's of Hollywood, catalog, vol. 70, Issue 356, Version 0600, ©1990, p. 68: "Wedding Surprise".

Primary Examiner—Robert A. Hafer
Assistant Examiner—David J. Kenealy
Attorney, Agent, or Firm—David Pressman

[57] ABSTRACT

A force-sensitive sound-playing condom comprising: a condom body (10) having a distal end and a proximal end, and a miniature force-sensitive sound-playing unit (14) attached to the condom at its proximal end. The proximal end of the condom is made in the form of a semirigid rim (12) having a lower part with an opening (16) coinciding with the cavity of the condom, and an upper part extending radially upwardly from the body of the condom and supporting the sound-playing unit (14). The latter contains a chip-controlled piezoelectric sound transducer which plays a melody or voiced message when during intercouse the contacts (28 and 30) of the sound-playing unit (14) are closed and the transducer is activated.

19 Claims, 1 Drawing Sheet

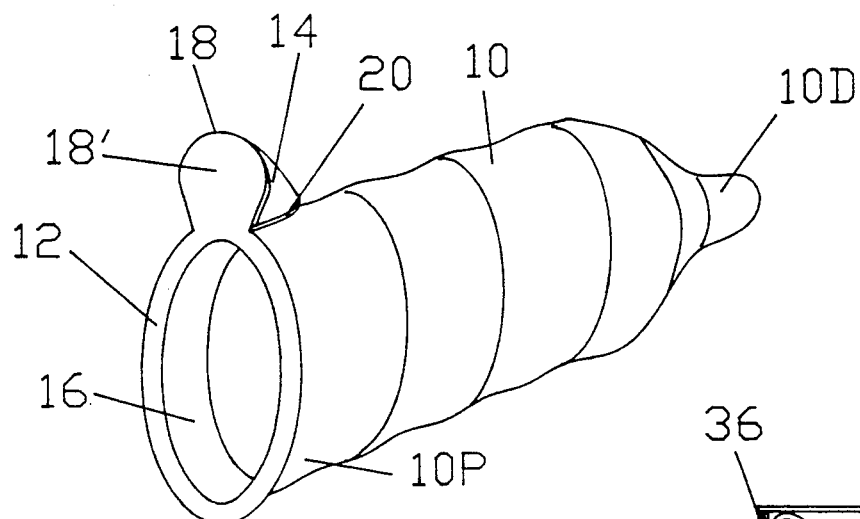
FIG.1
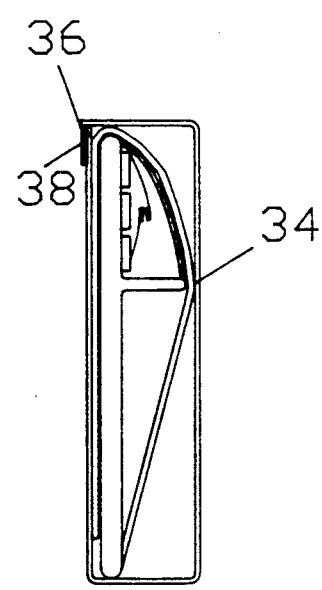
FIG.3
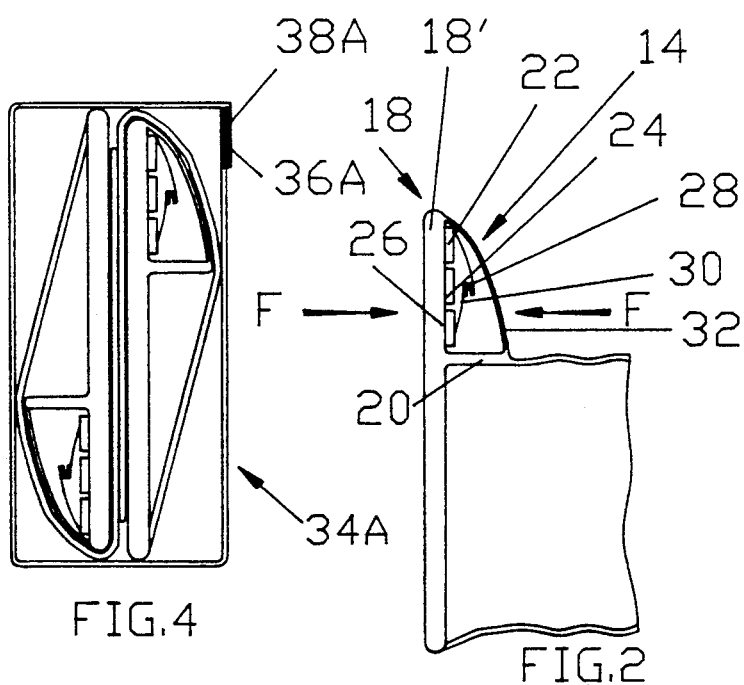
FIG.4
FIG.2

FORCE-SENSITIVE, SOUND-PLAYING CONDOM

BACKGROUND

1. Field of the Invention

The present invention relates to the field of contraceptives, particularly to condoms, and more particularly to a condom which provides entertainment and has an amusement feature.

2. Description of Prior Art

Many different kinds of contraceptive means, such as condoms, exist. They are all designed to function as methods of birth control and disease-prevention. They operate satisfactorily for these purposes, but many persons who engage in coitus dislike using them because they reduce sensitivity, interrupt coitus, and are bothersome to don.

OBJECTS AND ADVANTAGES OF THE INVENTION

It is therefore an object of the invention to provide a condom which users will like to use. Other objects are to provide a condom which provides amusement, which will not interfere with coitus, which has value as a fun gift, which can incorporate musical compositions of the user's choice according to the occasion, and which has a commercial value by being amusing, entertaining, unusual, and capable of producing a surprise effect. Further advantages and features of the invention will become apparent from a consideration of the ensuing description and drawings.

BRIEF DESCRIPTION OF DRAWINGS

FIG. 1 is a perspective view of a condom of the present invention.

FIG. 2 is a side view of a proximate portion of the condom illustrating a connection of a mechanism to the rim of the condom.

FIG. 3 is a sectional view of the condom in its package.

FIG. 4 is a sectional view of a similar package, containing two such condoms.

REFERENCE NUMERALS USED IN THE DRAWINGS AND DESCRIPTION

10—condom body
10P—proximal end of the condom
10D—distal end of the condom
12—rim
14—music-playing unit
16—opening
18—upper extension
18'—base
20—lip
22—piezoelectric sound transducer
24—chip
26—power source
28, 30—contacts
32—protective shield
34, 34a—packaging container
36, 36a—sealed flap
38—sealant

FIGS. 1 AND 2 — DETAILED DESCRIPTION OF CONDOM

A force-sensitive sound-playing condom according to the invention is shown in the attached drawings, wherein FIG. 1 is a perspective view of a force-pressure sound-playing condom and FIG. 2 is a side view of the proximate portion of the condom illustrating the connection of the sound-playing mechanism to the rim of the condom. FIG. 1 shows a force-sensitive, sound-playing condom; it consists essentially of a conventional condom body 10 of latex, having a proximal end 10P and a distal end 10D, and a reinforced or rolled rim 12. Rim 12 is semi-rigid and has an opening 16 coinciding with the cavity of the condom. Extending from one portion of rim 12 is an upper extension 18. Extension 18 projects radially upwardly from the body of the condom and supports a music- or sound-playing unit 14.

Rim 12 with extension 18 has a figure-eight shape (upper loop closed) when seen from the proximal end. It is made of rubber which may be reinforced internally by a stronger plastic core (not shown). The upper part of extension 18 is solid, forming a base 18' (FIG. 2) which is molded integrally with condom 10 and rim 12, but is of thicker latex than body 10.

In order to hold base 18' upright and coplanar with rim 12, a short lip 20 is formed as the extension of the partition between the round portions of the figure-eight structure, extending a short distance distally, parallel to the side wall of the condom. Lip 20 may have a length of about 20-30 mm and may have a partly-circular, cross-sectional shape matching that of rim 12.

As shown in FIG. 2, base 18' supports elements of a standard miniature musical unit 14 which is known per se and the structure of which is beyond the scope of the invention.

As shown schematically in FIG. 2, such a unit usually consists of a miniature piezoelectric sound transducer 22, a microchip 24 which controls the operation of transducer 22, a power-supplying dry-cell battery 26, and a switch comprising electrical contacts 28 and 30, which, when closed, complete an appropriate circuit (not shown) from battery 26 to microchip 24. When energized, microchip 24 will cause transducer 22 to emit a predetermined melody, or a voice message, such as a health warning (in case transducer 22 is a speaker). The circuit of musical unit 14, or chip 24, also incorporates a monostable multivibrator which controls an electronic bypass switch for contacts 28 (not shown) which ensures that current will be supplied to chip 24 for a predetermined period of time (for example, 10 seconds), so that the music continues to play even if contacts 28 are opened. This will cause the music or voice to play even if contact is intermittent, until the next contact takes place.

The music or voice message may be played once (e.g., an overture or melody may be played for about 20 seconds), or it may be repeated continuously for several minutes to coincide with the duration of coitus. A voiced message may be a warning about safe sex, or a compliment to the couple for using a condom. Suitable melodies (if music is played) may be *The 1812 Overture*, "*The Ode to Joy*" from Beethoven's *Ninth Symphony*, the song, "*Happy Birthday To You*," "*The Anniversary Waltz*," or any popular love song.

It is understood that all elements are interconnected through an appropriate fine wiring or a printed circuit (not shown) mounted on base 18'.

In order to protect the unit from mechanical damage and random completion of the circuit through contacts 28, unit 14 is covered with a protective shield 32. Shield 32 can be made of semirigid rubber or plastic, stretched tightly to provide adequate rigidity against sudden engagement of contacts 28 and 30, but also having sufficient elasticity to ensure such contact when a force F (FIG. 2) is applied to the external surface of shield 32 from the distal side. Shield 32 is stretched from the distal end of lip 20 toward the upper edge of base 18' and is seated so that unit 14 is encapsulated. Since base 18' is installed in a cantilever manner and is made of resilient material, and since upper extension 18 is rigid, contacts 28 and 30 will also be activated if force F is applied from the proximal direction, or from both directions.

A force F sufficient to bring contacts 28 and 30 into engagement may be about 5-10 g.

The inside of condom 10 is lubricated in a conventional manner to facilitate donning.

A typical sound-producing unit 14 suitable for the purposes of the invention may have overall dimensions within the range of 7 to 20 mm.

FIGS. 3 AND 4 —PACKAGING

The condom is shown in packaged form in FIG. 3. Unlike conventional condoms, the present condom cannot be simply rolled, because its switch is highly sensitive to pressure. Thus the body of the condom is completely wrapped around musical unit 14 and rim 12, and sealed inside a package 34. Alternatively, the body of condom 10 may be folded against rim 12. The product is then packed in a rigid boxlike container 34. Container 34 has an upper foldable flap 36, the free end of which is sealed, for example with a layer of a sealant 38, to ensure the sterility of the product in transportation and storage. Such packaging maintains contacts 28 and 30 disengaged.

Package 34 may be molded from rigid plastic and may have the following dimensions: 44×45×20 mm, or 45×20 mm, if circular. Although only one condom is shown in FIG. 3, it is understood that, as the back surface of the rim 12 and base 18' are coplanar, lying flat, it may be convenient to package two condoms in a back-to-back position in a single package as shown in FIG. 4.

The condom is mass produced and hence is inexpensive to manufacture. For this reason, as well as for health reasons, it should be disposed of after a single use.

The life of battery 26 may be indicated on package 34.

OPERATION

In order to use the condom, the user opens package 34 by unsealing flap 36 and removing wrapped condom 10. He then unwraps or unfolds the condom and slides it onto his erect penis. The lubricant inside the condom facilitates this operation.

During intercourse, the contact between the suprapubic genital areas of the couple will create forces F sufficient to engage contacts 28 and 30, completing the circuit. Power will pass from power source 26 to chip 24, and thus cause transducer 22 to produce sounds, e.g., music, or a voiced message. This message or music may warn, compliment, stimulate, entertain, or surprise the couple. The multivibrator in chip 24 ensures the continuation of music for a predetermined period of time, so that the melody will play once or repeatedly during intercourse.

Upper extension 18 will not interfere with coitus since it will be sandwiched between the suprapubic areas.

SUMMARY, RAMIFICATION, SCOPE

Thus, it has been shown that the condom of the invention provides a contraceptive combined with an amusing device, i.e., a force-sensitive sound-playing mechanism which is activated by the application of pressure during the use of the condom. The sound-playing condom is sensitive to slight pressure. The music playing unit is supported in such a manner as to not interfere with intercourse. The musical mechanism is protected by being entirely covered with a protective shield. It may have value as a fun gift incorporating other musical compositions of the user's choice according to the occasion, and may have further commercial value being amusing, entertaining, unusual, and capable of producing a surprise effect.

Although the force-sensitive sound-playing condom has been shown and described in the form of one specific embodiment, this embodiment, its parts, materials, and configurations have been given only as examples, and many other modifications of sound-playing condoms are possible. For example, rim 12 and extension 18 may have a shape other than a figure-eight; all components of musical unit 1 4 may be embedded entirely in resilient plastic, leaving only space between contacts 28 and 30 so that all of the contacts, excepting the exposed contacting portions, are embedded and thus maintained in an open state by the resiliency of the embedded mass. The musical units themselves may have different forms, dimensions, and configurations. There may be a range of musical or other sound selections which may be chosen or combined by the user. The rim and base may be reinforced by a wire. Various parts of the musical circuit may assume lateral positions around the rim, i.e., piezoelectric sound transducers may be displaced laterally on one side, while the chip may be arranged on the other side. Similarly, the package itself may take different forms and show a variety of messages. Although in the preferred embodiment shown above, it is a disposable condom, the musical unit may be made in such a way that it can be detached and readily disconnected or connected onto other condoms by means such as adhesive tapes. In that case the package might contain, for example, ten condoms and a single musical unit. A speaker can be used instead of a piezoelectric transducer. The condom will operate in homosexual as well as heterosexual intercourse. In lieu of mechanical contacts 28 and 30, a strain-gauge-type activator or any other type of activator may be employed.

Therefore, the scope of the invention should be determined, not by the example given, but by the appended claims and their legal equivalents.

What I claim is:

1. A force-sensitive sound-playing condom, comprising:
   a condom body, and
   force-sensitive sound-playing means for emitting a predetermined sound, said force-sensitive sound-playing means being attached to said condom body,
   said condom being donnable upon an erect penis without activating said force-sensitive sound-playing means,
   said force-sensitive sound-playing means being designed to emit said predetermined sound in response to a predetermined external force created during the act of sexual intercourse.

2. The force-sensitive sound-playing condom of claim 1 wherein said condom body has a distal end and a proximal end and wherein said means is attached to said proximal end.

3. The force-sensitive sound-playing condom of claim 2 wherein said proximal end of said condom body has a semi-rigid rim having an opening coinciding with the cavity of said condom body, said means extending radially upwardly from said condom body.

4. The force-sensitive sound-playing condom of claim 3 wherein said force-sensitive sound-playing means is a miniature device having a power supply source, a piezoelectric sound transducer, a pair of force-sensitive contacts which are closed when said predetermined force is applied to at least one of said contacts, and a chip with elements which control operation of said music playing means when said contacts are closed.

5. The force-sensitive sound-playing condom of claim 4 wherein said rim is solid and said means has a semi-rigid protective cover which possesses flexibility sufficient to bring one of said contacts into engagement with the other when said predetermined force is applied to one of said contacts.

6. The force-sensitive sound-playing condom of claim 5 wherein said condom body and said protective cover are integrally molded.

7. The force-sensitive sound-playing condom of claim 5 wherein said predetermined force is 5 grams or greater.

8. The force-sensitive sound-playing condom of claim 3 wherein said means has a lip distally extending from said semi-rigid rim, said lip having a length of about 20-30 mm.

9. The force-sensitive sound-playing condom of claim 3, further including a rigid boxlike packaging container having means for sealing said condom in a state in which a part of said condom body is wrapped around said sound-playing means and said rim.

10. A force-sensitive sound-playing condom, comprising:
   a condom body having a distal end and a proximal end, said proximal end being made in the form of a semi-rigid rim having an opening coinciding with the cavity of said condom,
   force-sensitive sound-playing means for emitting a predetermined sound, said force-sensitive sound-playing means being attached to said proximal end of condom body,
   said force-sensitive sound-playing means extending radially upwardly from said proximal end of said condom body,
   said condom being donnable upon an erect penis without activating said force-sensitive sound-playing means,
   said force-sensitive sound-playing means being designed to emit said predetermined sound in response to a predetermined external force created during the act of sexual intercourse.

11. The force-sensitive sound-playing condom of claim 10 wherein said sound-playing means is a miniature device having a source of power, a piezoelectric sound transducer, a pair of force-sensitive contacts which are closed when a pressure is applied to at least one of said contacts, and a chip with elements which control operation of said sound-playing means when said contacts are closed.

12. The force-sensitive sound-playing condom of claim 11 wherein said rim is solid and said force-sensitive sound-playing means has a semi-rigid protective cover which possesses flexibility sufficient to bring one of said contacts into engagement with the other when said predetermined force is applied to one of said contacts, said means and said rim having coplanar surfaces.

13. The force-sensitive sound-playing condom of claim 12 wherein said predetermined force is 5 grams or greater.

14. The force-sensitive sound-playing condom of claim 10 wherein said means has a lip distally extending from said rim, said lip having a length of about 20 to 30 millimeters.

15. The force-sensitive sound-playing condom of claim 10, further including a rigid boxlike packaging container having means for sealing having means for sealing said condom in a state in which a part of said condom body is wrapped around said sound-playing means and said rim.

16. A force-sensitive sound-playing condom, comprising:
   a condom body having a distal end and a proximal end, and
   force-sensitive sound-playing means attached to said proximal end of said condom body,
   said proximal end being made in the form of a semi-rigid rim having an opening coinciding with the cavity of said condom,
   said force-sensitive sound-playing means extending radially upwardly from said proximal end of said condom body,
   said force-sensitive sound-playing means comprising a miniature device having a source of energy, a piezoelectric sound transducer, a pair of force-sensitive contacts, and a chip with elements which control operation of said sound-playing means when said contacts are closed,
   said condom being donnable upon an erect penis without activating said force-sensitive sound-playing means,
   said pair of force-sensitive contacts being positioned so that at least one of said pair of contacts receives a predetermined external force created during the act of sexual intercourse, said pair of contacts closing in response to said at least one of said contacts receiving said predetermined external force, said chip being connected to said source of energy when said pair of contacts close so that said piezoelectric sound transducer will emit a predetermined sound during said act of sexual intercourse.

17. The force-sensitive sound-playing condom of claim 16 wherein said rim is solid and said means has a semi-rigid protective cover which possesses flexibility sufficient to bring one of said pair of contacts into engagement with the other when said predetermined force is applied to said cover, said semi-rigid cover and said means having surfaces which are flat and coplanar.

18. The force-sensitive sound-playing condom of claim 17 wherein said force-sensitive sound-playing means has a lip distally extending from said semi-rigid rim, said lip having a length of about 20-30 mm.

19. The force-sensitive sound-playing condom of claim 16, further including a rigid boxlike packaging container having means for sealing said condom in a state in which a part of said condom body is wrapped around said sound-playing means and said rim.

* * * * *